United States Patent [19]

Hirai et al.

[11] 4,159,374

[45] Jun. 26, 1979

[54] TRIAZOLYLPHENYL KETONE DERIVATIVES AND PRODUCTION THEREOF

[75] Inventors: Kentaro Hirai, Kyoto; Hirohiko Sugimoto, Ikeda, both of Japan

[73] Assignee: Shionogi & Co., Ltd., Osaka, Japan

[21] Appl. No.: 803,303

[22] Filed: Jun. 3, 1977

[30] Foreign Application Priority Data

Jun. 4, 1976 [JP]  Japan ................................. 51-65869

[51] Int. Cl.² .............. C07D 249/10; C07D 401/06; C07D 401/10; C07D 413/06
[52] U.S. Cl. ............................. 544/132; 260/308 R; 260/326 N; 260/326.5 E; 260/558 H; 424/248.54; 424/263; 424/267; 544/82; 544/124; 544/130; 544/131; 544/162; 546/187; 546/193; 546/194; 546/210; 546/275; 546/276; 560/350
[58] Field of Search ......... 260/308 R, 293.63, 293.67, 260/293.69, 293.71, 295 AM; 544/82, 124, 130, 131, 132; 546/187, 194, 193, 210, 276

[56] References Cited

U.S. PATENT DOCUMENTS

| | | | |
|---|---|---|---|
| 3,862,171 | 1/1975 | Gagneux et al. ............. | 260/308 R |
| 3,870,714 | 3/1975 | Gagneux et al. ............. | 260/308 R |
| 3,993,660 | 11/1976 | Hester ......................... | 260/308 R |
| 4,007,219 | 2/1977 | Hassall et al. ............... | 548/324 |

*Primary Examiner*—Alton D. Rollins
*Attorney, Agent, or Firm*—Wenderoth, Lind & Ponack

[57] ABSTRACT

Triazolyl ketone derivatives of the formula:

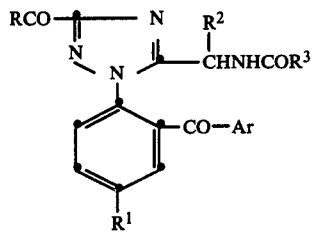

(wherein R represents lower alkoxy or the group

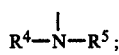

$R^4$ and $R^5$ each represents hydrogen, lower alkyl, or 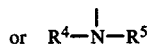

represents hetero ring selected from pyrrolidino, piperidino, and morpholino; $R^1$ represents halogen or nitro; $R^2$ represents hydrogen or lower alkyl; $R^3$ represents lower alkyl, phenyl, or the group

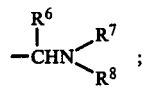

$R^6$ represents hydrogen, lower alkyl, or benzyl; $R^7$ and $R^8$ each represents hydrogen, lower alkyl, or

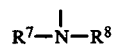

represents hetero ring selected from pyrrolidino, piperidino, and morpholino; and Ar represents phenyl, o-halogenophenyl, or 2-pyridyl) and their pharmaceutically acceptable acid addition salts, being useful as anxiolytics, hypnotics, anticonvulsants, muscle relaxants, or their synthetic intermediates, are prepared by several routes.

17 Claims, No Drawings

TRIAZOLYLPHENYL KETONE DERIVATIVES AND PRODUCTION THEREOF

The present invention relates to triazolylphenyl ketone derivatives of the formula:

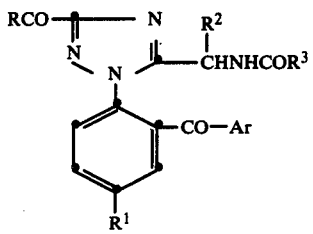

(wherein R represents lower alkoxy or the group

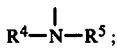

$R^4$ and $R^5$ each represents hydrogen, lower alkyl, or

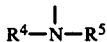

represents hetero ring selected from pyrrolidino, piperidino, and morpholino; $R^1$ represents halogen or nitro; $R^2$ represents hydrogen or lower alkyl; $R^3$ represents lower alkyl, phenyl or the group

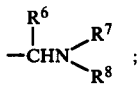

$R^6$ represents hydrogen, lower alkyl, or benzyl; $R^7$ and $R^8$ each represents hydrogen, lower alkyl, or

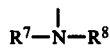

represents hetero ring selected from pyrrolidino, peperidino, and morpholino; and Ar represents phenyl, o-halogenophenyl, or 2-pyridyl) and their pharmaceutically acceptable acid addition salts, being useful as anxiolytics, hypnotics, anticonvulsants, muscle relaxants, or their synthetic intermediates.

The definition of the substitutent used in the invention can be complemented as follows: The lower alkoxy involves methoxy, ethoxy, propoxy, i-propoxy, and butoxy; the lower alkyl involves methyl, ethyl, propyl, i-propyl, butyl, i-butyl, t-butyl, and pentyl; the halogen involves chlorine, bromine, fluorine, and iodine.

The acid addition salts means pharmaceutically acceptable inorganic or organic acid addition salts, and illustratively involve salts of inorganic acid (e.g. hydrochloric acid, nitric acid, hydrobromic acid, sulfuric acid, phosphoric acid, thiocyanic acid) and salts of organic acid (e.g. acetic acid, oxalic acid, succinic acid, maleic acid, malic acid, citric acid, tartaric acid, phthalic acid, methanesulfonic acid).

The triazolyl ketone derivatives (I) involve firstly a compound of the formula:

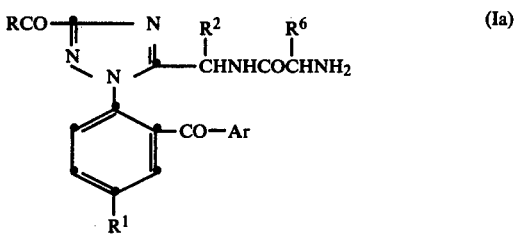

(wherein R, $R^1$, $R^2$, $R^6$, and Ar each is as defined above), which can be prepared by subjecting a compound of the formula:

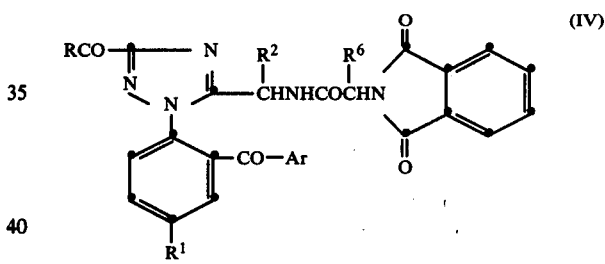

(wherein R, $R^1$, $R^2$, $R^6$, and Ar each is as defined above) to hydrazinolysis in an inert solvent. The hydrazinolysis is effected by treating with hydrazine hydrate in an inert solvent (e.g. dimethylformamide, hexamethylphosphoric triamide, pyridine, benzene, methanol, ethanol, their mixture) at room temperature or under heating. The starting compound (IV) is obtained from the compound (II) as follows:

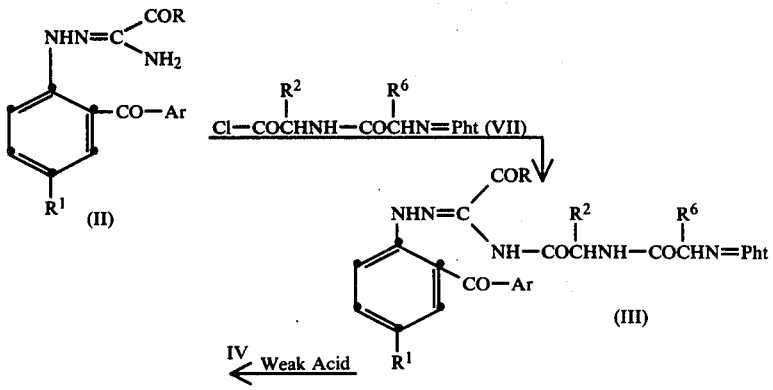

(wherein Pht represents phthalyl; R, R¹, R², R⁶, and Ar each is as defined above.)

The starting compound (IV) is also prepared by reacting a compound of the formula:

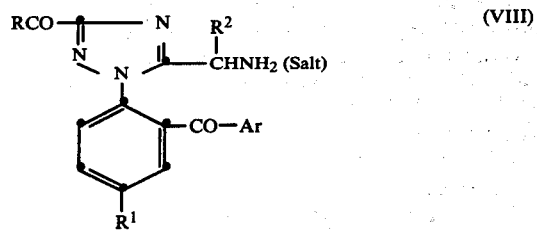
(VIII)

(wherein R, R¹, R², and Ar each is defined above) with a compound of the formula:

(IX)

(wherein R⁶ and Pht each is as defined above) in the presence of a base such as alkali carbonate or triethylamine.

Another subgeneric compound of this invention is represented by the formula:

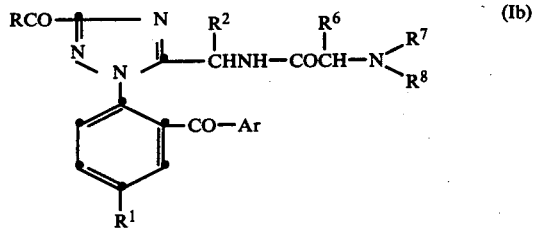
(Ib)

(wherein R represents lower alkoxy, di(lower)alkylamino, pyrrolidino, piperidino, or morpholino; R¹ represents halogen; R² represents hydrogen or lower alkyl; R⁶ represents hydrogen, lower alkyl, or benzyl

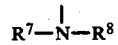

represents amino, (lower)alkylamino, di(lower)alkylamino, pyrrolidino, piperidino, or morpholino; and Ar represents phenyl, o-halo-phenyl, or 2-pyridyl), and the compound (Ib) can be prepared by reacting a compound of the formula:

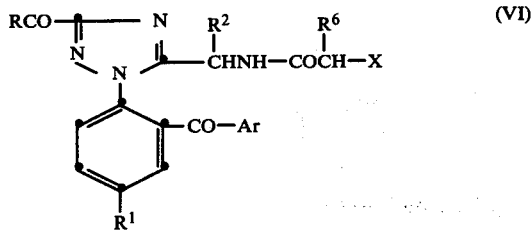
(VI)

(wherein X represents halogen; R, R¹, R², R⁶, and Ar each is as defined above) with a compound of the formula:

(X)

(wherein R⁷ and R⁸ each is as defined above) in an inert solvent (e.g. chloroform, methanol, dimethylformamide, benzene, dioxane, pyridine, their mixture). This reaction may be carried out at room temperature or under heating. The starting compound (VI) can be readily derived from the compound (VIII) by treating with, for example, chloroacetyl chloride.

A further subgeneric compound of the present invention is shown by the following formula:

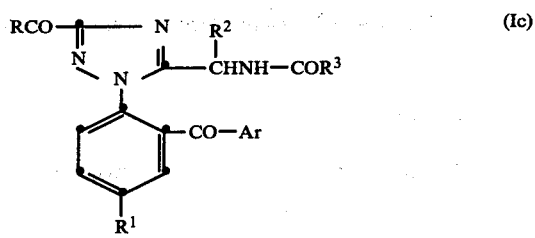
(Ic)

(wherein R³ represents lower alkyl or phenyl; R, R¹, R², and Ar each is as defined above) and the compound (Ic) can be prepared by treating the compound (VIII) with a corresponding acylating agent (e.g. acid anhydride, acid halide) in the presence or absence of an inert solvent (e.g. water, methanol, ethanol, dimethylformamide, chloroform, ether dioxane, methylene chloride, or their mixture) at room temperature or under cooling or heating.

The original compound (II) can be prepared by ammonolysis, aminolysis, or by ester exchange from, for example, 1-[2-(2-chlorobenzoyl)-4-chlorophenyl]-2-(1-amino-1-ethoxycarbonylmethylene)hydrazine (IIa) [Japanese Patent Kokai 101396/1974]. For example, IIa is reacted with dimethylamine to give 1-[2-(2-chlorobenzoyl)-4-chlorophenyl]-2-(1-amino-1-dimethylcarbamoylmethylene)hydrazine (IIb):

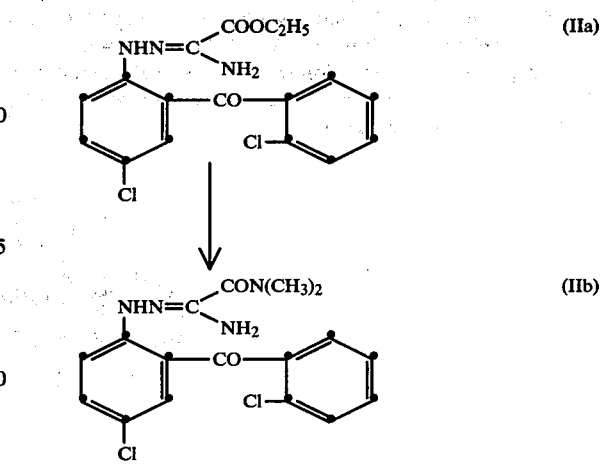

Still, another original compound (II), in particular 1-(2-benzoyl-4-chlorophenyl)-2-(1-amino-1-dimethylcarbamoyllmethylene)hydrazine (IIc) is prepared as follows:

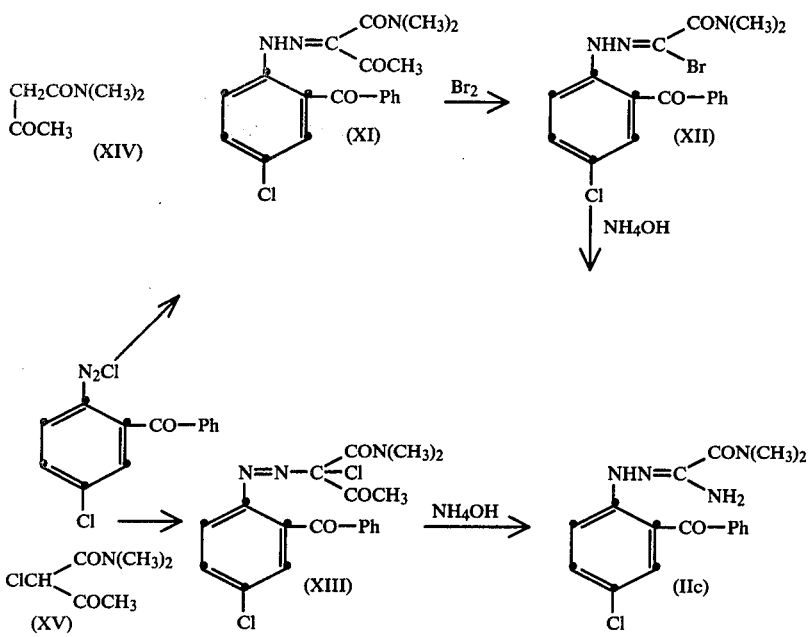

Thus, the compound (IIc) is prepared by reacting a diazonium salt of 2-amino-5-chlorobenzophenone with the compound (XIV), brominating the resulting compound (XI) and treating with aqueous ammonia; or reacting a diazonium salt of 2-amino-5-chlorobenzophenone with the compound (XV) and treating the resulting product (XIII) with aqueous ammonia.

The objective compound (Ia) involves illustratively
5-chloro-2(3-dimethylcarbamoyl-5-glycylaminomethyl-1H-1,2,4-triazol-1-yl)benzophenone;
2',5-dichloro-2-(3-dimethylcarbamoyl-5-glycylaminomethyl-1H-1,2,4-triazol-1-yl)benzophenone;
2'-fluoro-5-chloro-2-(3-dimethylcarbamoyl-5-glycylaminomethyl-1H-1,2,4-triazol-1-yl)benzophenone;
5-chloro-2-[3-dimethylcarbamoyl-5-(1-glycylaminoethyl)-1H-1,2,4-triazol-1-yl]benzophenone;
2',5-dichloro-2-(3-dimethylcarbamoyl-5-L-leucylaminomethyl-1H-1,2,4-triazol-1-yl)benzophenone; and
2',5-dichloro-2-(3-dimethylcarbamoyl-5L-phenylalanylaminomethyl-1H-1,2,4-triazol-1-yl)benzophenone;
the compound (Ib) involves illustratively
2',5-dichloro-2-(3-pyrrolidinocarbonyl-5-glycylaminomethyl-1H-1,2,4-triazol-1-yl)benzophenone;
2',5-dichloro-2-(3-morpholinocarbonyl-5-glycylaminomethyl-1H-1,2,4-triazol-1-yl)benzophenone;
4-bromo-2-(2-picolinoyl)-1-(3-pyrrolidinocarbonyl-5-glycylaminomethyl-1H-1,2,4-triazol-1-yl)benzene;
2',5-dichloro-2-(3-ethoxycarbonyl-5-glycylaminomethyl-1H-1,2,4-triazol-1-yl)benzophenone;
2',5-dichloro-2-[3-dimethylcarbamoyl-5-(2-dimethylaminoacetyl)aminomethyl-1H-1,2,4-triazol-1-yl]benzophenone;
2',5-dichloro-2-[3-dimethylcarbamoyl-5-(2-pyrrolinoacetyl)aminomethyl-1H-1,2,4-triazol-1-yl]benzophenone;
2',5-dichloro-2-[3-dimethylcarbamoyl-5-(2-methylaminoacetyl)aminomethyl-1H-1,2,4-triazol-1-yl]benzophenone; and
the compound (Ic) involves
2',5-dichloro-2-(3-dimethylcarbamoyl-5-acetamidomethyl-1H-1,2,4-triazol-1-yl)benzophenone;
2',5-dichloro-2-(3-dimethylcarbamoyl-5-benzamidomethyl-1H-1,2,4-triazol-1-yl)benzophenone;
2',5-dichloro-2-(3-dimethylcarbamoyl-5-i-propionamidomethyl-1H-1,2,4-triazol-1-yl)benzophenone.

Thus obtained triazolylphenyl ketone derivatives (I) or their pharmaceutically acceptable acid addition salts are useful as anxiolytics, sedatives, anticonvulsives, hypnotics, muscle relaxants, or their synthetic intermediates. For example, 2',5-dichloro-2-(3-dimethylcarbamoyl-5-glycylaminomethyl-1H-1,2,4-triazol-1-yl)benzophenone hydrochloride shows $ED_{50}$ 0.52 mg/kg (mouse, per os.) in anticonvulsive activity due to pentylenetetrazole; and $LD_{50} > 1500$ mg/kg (mouse, per os.) in acute toxicity test. Other compounds (I) show similar pharmacological activities.

The triazolyphenyl ketone derivatives and their pharmaceutically acceptable acid addition salts are applied by either enteral or parenteral route singly or in combination with pharmaceutically suitable carriers such as wheat starch, corn starch, potato starch, gelatin, or other solid carriers, and liquid carriers such as gelatin, water, ethanol, glycerin. The choice of carriers is determined by the preferred route of administration, the solubility of the substance, and standard pharmaceutical practice. Examples of pharmaceutical preparations are tablets, capsules, pills, suspensions, syrups, powders, and solutions. These compositions can be prepared in a conventional manner, and the active compound (I) is orally administered to human adults in the order of about 0.2 mg to about 80 mg per day.

Presently-preferred and practical embodiments of the present invention are illustratively shown in the following examples.

EXAMPLE 1

(1) To a suspension of 1-[2-(2-chlorobenzoyl)-4-chlorophenyl]-2-(1-amino-1-ethoxycarbonylmethylene)hydrazine (24.9 g) in methanol (300 ml), excess of gaseous dimethylamine is introduced at room temperature, and the reaction mixture is allowed to stand overnight. After evaporating the solvent under reduced pressure, the residue is recrystallized from ethanol to give 1-[2-(2-chlorobenzoyl)-4-chlorophenyl]-2-(1-amino-1-dimethylcarbamoylmethylene)hydrazine (21.3 g) as reddish orange crystals melting at 150 to 151° C. The yield is 85.5%.

(2) A suspension of above products (5.7 g), phthalylglycyl-glycyl chloride (4.62 g), dimethylformamide (10 ml), tetrahydrofuran (100 ml), and potassium carbonate (1.24 g) is stirred at room temperature for 4 hours and allowed to stand overnight. The reaction mixture is neutralized with aqueous sodium bicarbonate and evaporated under reduced pressure to remove the solvent. The residue is shaken with ethyl acetate. The ethyl acetate layer is washed with water, dried and evaporated under reduced pressure to give a gelatinous material, which is mixed with acetic acid without purification and refluxed for 2 hours. The reaction mixture is evaporated under reduced pressure to remove acetic acid, and the residue is shaken with chloroform. The chloroform layer is washed with aqueous sodium bicarbonate and water in order, dried and evaporated to remove the chloroform. The residue is chromatographed on a column of silica gel, which is eluted with ethyl acetate. The eluate is evaporated to give 2′,5-dichloro-2-[3-dimethylcarbamoyl-5-(2-phthalamidoacetyl)aminomethyl-1H-1,2,4-triazol-1-yl]benzophenone (5.55 g), which is recrystallized from ethanol to give colorless needles melting at about 153° C.

(3) To a suspension of above product (4.42 g) in ethanol (50 ml), hydrazine hydrate (0.983ml) is added, and the resultant mixture is refluxed for 1 hour under heating. After cooling, the precipitated phthalyl hydrazide is filtered off, and the filtrate is evaporated under reduced pressure to remove the solvent. The residue is extracted with chloroform. The chloroform layer is washed with aqueous sodium bicarbonate and water in order, dried, and evaporated to remove the solvent. The residue is chromatographed on a column of silica gel, which is eluted with methanol. The eluate is evaporated to give crude product, which is treated with ethanolic hydrochloric acid. The hydrochloride is recrystallized from 95% ethanol to give 2′,5-dichloro-2-(3-dimethylcarbamoyl-5-glycylaminomethyl-1H-1,2,4-triazol-1-yl)benzophenone hydrochloride dihydrate as colorless needles initiating to melt at about 107° C. but showing no evident end melting point. The oxalate shows m.p. 180°–182° C. (decomp.).

EXAMPLE 2-7

Using the starting material (II), the reactions are effected as in Example 1, whereby the product (Ia) is obtained.

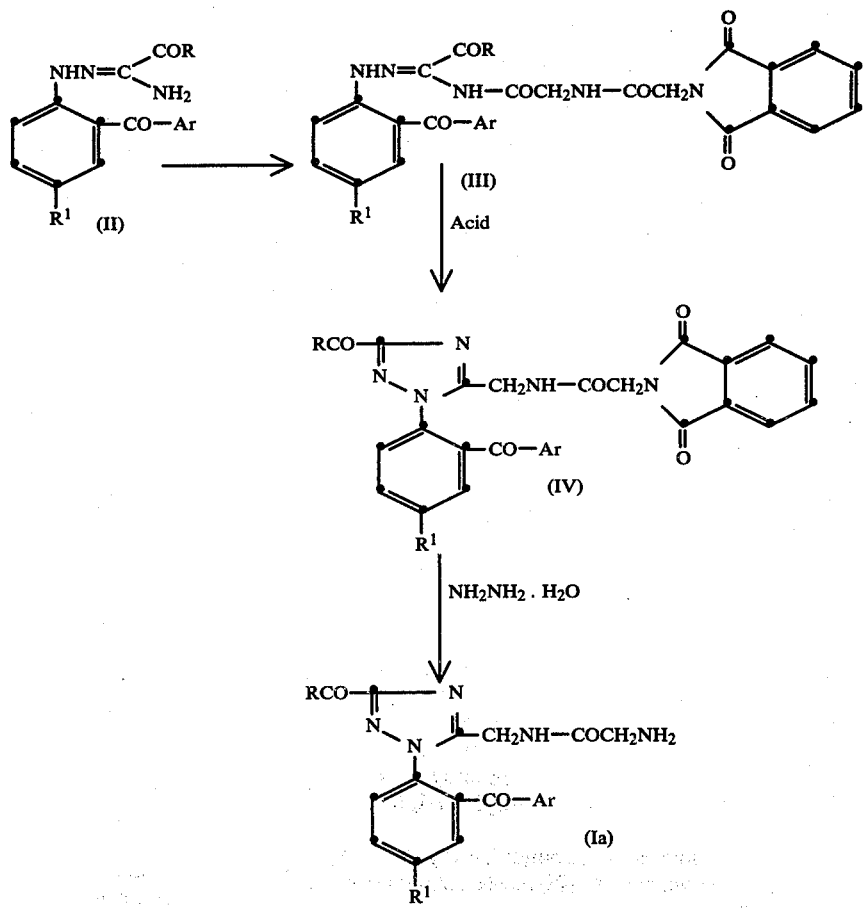

Table 1.

| Ex. No. | R | R¹ | Ar | II m.p.(°C.) | IV m.p.(°C.) | Ia m.p.(°C.) |
|---|---|---|---|---|---|---|
| 2 | Me₂N— | Cl | Ph | 167–169 | 214–216 | HCl, 247–250(d) |
| 3 | Me₂N— | Cl | o-F—Ph | 151–153 | 224–226 | HCl, 220–222(d) |
| 4 | pyrrolidin-1-yl | Cl | o-Cl—Ph | 172–174 | 160–165 | 130–132 |
| 5 | morpholin-4-yl | Cl | o-Cl—Ph | 186–187 | 204–205 (d) | HCl, 150 (d) Oxalate, 153–156(d) |
| 6 | pyrrolidin-1-yl | Br | 2-Py | 212–213 | 252–254 | 166–168 |
| 7 | Et—O— | Cl | o-Cl—Ph | 120–124 | 194–195 | HCl, 160(d) Oxalate, 202–203(d) |

Note:
The abbreviations in the table have each the following significance:
Me (Methyl group), Et (Ethyl group), Ph (Phenyl group), Py (Pyridyl group), d (decomposed).

EXAMPLE 8

(1) A solution of carbobenzoxy-L-alanine (4.48 g) in tetrahydrofuran (15 ml) is mixed with phosphorus pentachloride (4.58 g) to give a solution of carbobenzoxy-L-alanyl chloride in tetrahydrofuran, which is added to a solution of 1-(2-benzoyl-4-chlorophenyl)-2-(1-amino-1-dimethylcarbamoylmethylene)hydrazine (3.45 g) in tetrahydrofuran (70 ml) and dimethylformamide (20 ml). The resultant mixture is stirred at room temperature for 1 hour, mixed with potassium carbonate (1.38 g), stirred for 4 hours, and allowed to stand overnight. The reaction mixture is mixed with water and evaporated under reduced pressure to remove the solvents, and the residue is extracted with ethyl acetate. The organic layer is dried and evaporated to remove the ethyl acetate, whereby 1-(2-benzoyl-4-chlorophenyl)-2-[1-(carbobenzoxy-L-alanylamino)-1-dimethylcarbamoylmethylene]hydrazine is obtained as a residue. The residue is mixed with acetic acid (30 ml) without purification, and the resultant solution is refluxed for 2 hours under heating. The reaction mixture is evaporated under reduced pressure to remove the acetic acid. The residue is extracted with chloroform, and the chloroform layer is washed with aqueous sodium bicarbonate and water in order, dried and evaporated to remove the chloroform. The residue is chromatographed on a column of silica gel, which is eluted with ethyl acetate. The eluate is evaporated to give 5-chloro-2-[3-dimethylcarbamoyl-5-(1-carbobenzoxyaminoethyl)-1H-1,2,4-triazol-1-yl]benzophenone (1.4 g) as a gelatinous material.

(2) A mixture of above product (1.35 g) and 30% hydrogen bromide-acetic acid (4.5 ml) is stirred at room temperature for 1.5 hours. The reaction mixture is washed twice with ether. The obtained crude 5-chloro-2-[3-dimethylcarbamoyl-5-(1-aminoethyl)-1H-1,2,4-triazol-1-yl]-benzophenone hydrobromide is mixed with benzene (30 ml) and phthalylglycyl chloride (0.853 g), and the resultant mixture is stirred at room temperature for 5 minutes, mixed with dimethylformamide (10 ml) and stirred at room temperature for 4 hours. The reaction mixture is neutralized with aqueous sodium bicarbonate and shaken with ethyl acetate. The organic layer is dried and evaporated to remove the ethyl acetate. The residue is chromatographed on a column of silica gel, which is eluted with ethyl acetate. The eluate is evaporated to give 5-chloro-2-[3-dimethylcarbamoyl-5-(1-phthalylglycylaminoethyl)-1H-1,2,4-triazol-1-yl]-benzophenone (0.455 g), which is recrystallized from ether to give colorless needles initiating to melt at about 120° C. but showing no evident final melting point.

(3) A mixture of above product (0.351 g), ethanol (5 ml) and hydrazine hydrate (0.078 ml) is refluxed for 1 hour under heating. After cooling, the reaction mixture is filtered to remove insoluble materials. The filtrate is evaporated under reduced pressure to remove the solvent, and the residue is extracted with chloroform. The chloroform layer is washed with aqueous sodium bicarbonate and water in order, dried and evaporated to remove the chloroform. The residue is dissolved in ethanol, mixed with ethanolic hydrochloric acid, and then treated with ether to give 5-chloro-2-[3-dimethylcarbamoyl-5-(1-glycylaminoethyl)-1H-1,2,4-triazol-1-yl]-benzophenone hydrochloride (0.24 g) as crystals initiating to melt at 155° C. but showing no evident final melting point: $[\alpha]_D^{24.5} -54.7° \pm 0.9°$ (EtOH).

EXAMPLE 9–10

Using the following starting material (IIa), the reaction is carried out as in Example 8, whereby the corresponding product (Ia) is obtained:

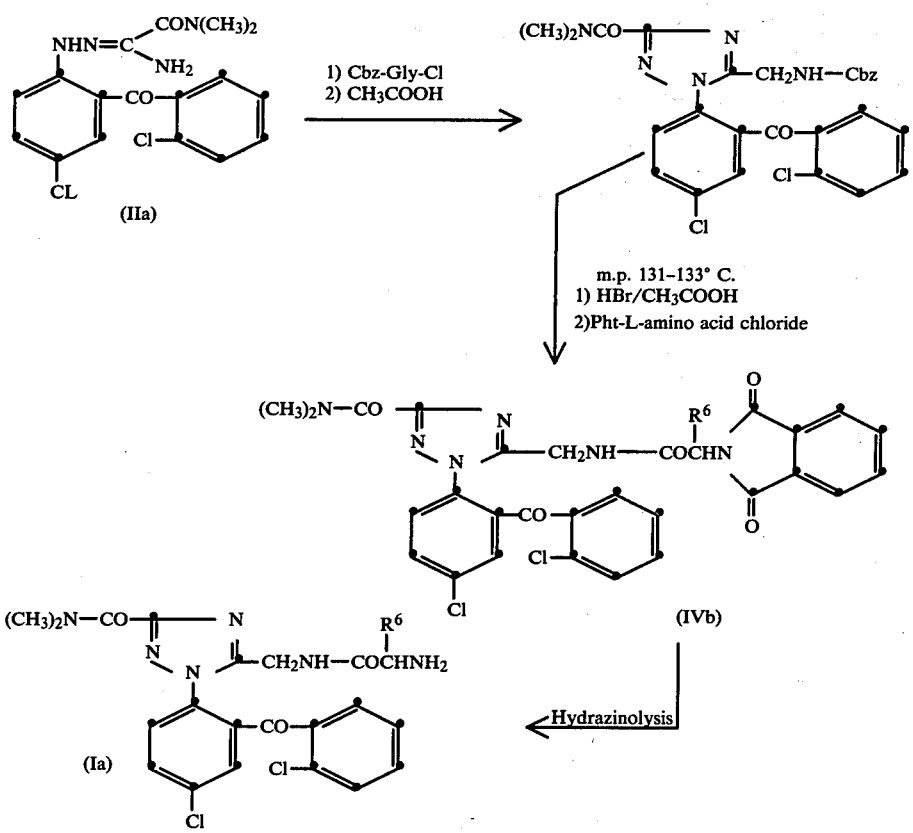

Table 2.

| Ex. No. | R⁶ | IVb m.p.(°C.) | Ia m.p.(°C.) | $[\alpha]_D^{22}$(EtOH) |
|---|---|---|---|---|
| 9 | i-Bu | 161–164 | 120 ca. | +1.0±0.4° |
| 10 | Bz | 162–166 | 135 ca. | +7.1±0.5° |

Note:
The abbreviations in the table have the following significance.
Bu (Butyl group), Bz (Benzyl group), i- (iso- ), Cbz (Carbobenzoxy group).

EXAMPLE 11

(1) A mixture of 2',5-dichloro-2-(3-dimethylcarbamoyl-5-carbobenzoxyaminomethyl-1,2,4-triazol-1-yl)benzophenone (3.6 g) and 30% hydrogen bromide-acetic acid (9 ml) is stirred at room temperature for 2 hours. The reaction mixture is mixed with ether, and the precipitate is isolated by decantation and washed thrice with ether, whereby 2',5-dichloro-2-(3-dimethylcarbamoyl-5-aminomethyl-1,2,4-triazol-1-yl)-benzophenone hydrobromide is obtained. This hydrobromide (1.2 g) is added to a solution of chloroacetyl chloride (1.2 g) in benzene (40 ml) to give a solution, which is mixed with dimethylformamide (20 ml). The resultant mixture is stirred at room temperature for 3 hours. The reaction mixture is mixed with ethyl acetate and neutralized with aqueous sodium bicarbonate. The organic layer is separated, washed with water, dried, and evaporated under reduced pressure to remove the solvent. The residue is treated with ethanol/n-hexane to give 2',5-dichloro-2-[3-dimethylcarbamoyl-5-(2-chloroacetylamino)methyl-1,2,4-triazol-1-yl]-benzophenone (12.9 g), which is recrystallized from ethyl acetate to give colorless needles melting at 80°–82° C.

(2) To a solution of above product (0.5 g) in chloroform (6 ml) and methanol (3 ml), 50% aqueous dimethylamine solution (0.2 g) is added, and the resultant mixture is allowed to stand 3 days. The reaction mixture is evaporated under reduced pressure to remove the solvents, and the residue is extracted with methylene chloride. The organic layer is washed with water, dried and evaporated to remove the methylene chloride. The residue is chromatographed on a column of silica gel, which is eluted with ethyl acetatemethanol (4:1). The eluate is evaporated to give a viscous oil, which is treated with ethyl acetate/n-hexane to give 2',5-dichloro-2-[3-dimethylcarbamoyl-5-(2-dimethylaminoacetylamino)methyl-1,2,4-triazol-1-yl]-benzophenone (0.2 g) as colorless needles melting at 122°–124° C.

EXAMPLE 12–14

Using the following starting material (V), the reaction is effected as in Example 11 (1), whereby the corresponding product (Ic) is obtained.

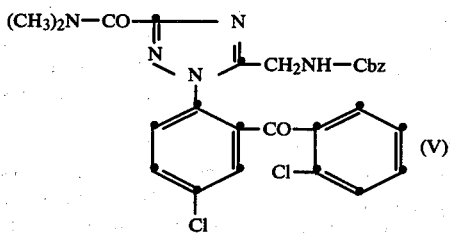

-continued

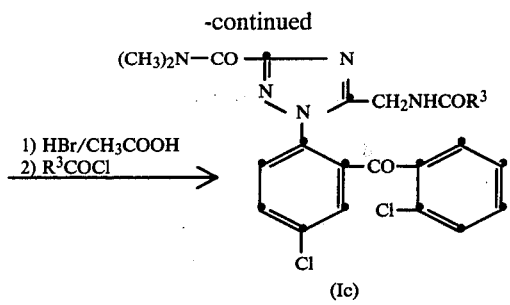

Table 3.

| Ex. No. | Ic R⁶ | m.p. (° C.) |
|---|---|---|
| 12 | Ph | 180–183 |
| 13 | i-Pr | 180–183 |
| 14 | Me | 118–120 |

Note:
The abbreviation in the table has the following significance.
Pr (Propyl).

EXAMPLE 15–16

Using the following starting material (VI), the reaction is effected as in Example 11 (2), whereby the corresponding product (Ib) is obtained.

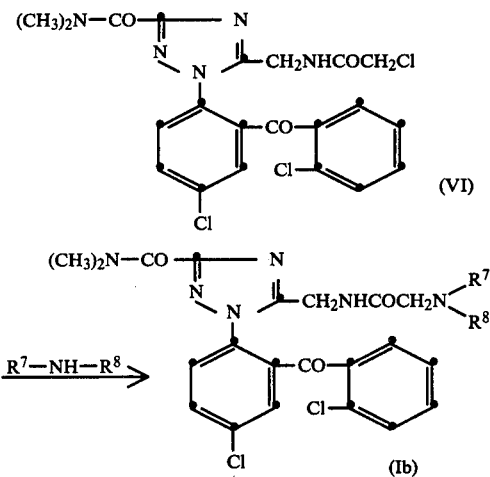

Table 4.

| Ex. No. | Ib R⁷—N—R⁸ | m.p. (° C.) |
|---|---|---|
| 15 |  | 119–122 |
| 16 | CH₃—N—H | 124–125 |

What is claimed is:
1. A compound of the formula:

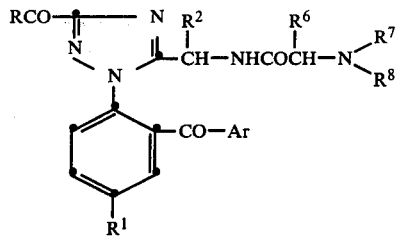

wherein R represents lower alkoxy, di(lower)alkylamino, pyrrolidino, piperidino, or morpholino; $R^1$ represents halogen; $R^2$ represents hydrogen or lower alkyl; $R^6$ represents hydrogen, lower alkyl, or benzyl;

$$R^7-\underset{|}{N}-R^8$$

represents amino, (lower)alkylamino, di(lower)alkylamino, pyrrolidino, piperidino, or morpholino; and Ar represents phenyl, o-halogenophenyl, or 2-pyridyl and its pharmaceutically acceptable acid addition salt.

2. A compound according to claim 1, in which R is dimethylamino and $$R^7-\underset{|}{N}-R^8$$

is amino.

3. A compound according to claim 2, namely 5-chloro-2-(3-dimethylcarbamoyl-5-glycylaminomethyl-1H-1,2,4-triazol-1-yl)benzophenone.

4. A compound according to claim 2, namely 2',5-dichloro-2-(3-dimethylcarbamoyl-5-glycylaminomethyl-1H-1,2,4-triazol-1-yl)benzophenone.

5. A compound according to claim 2, namely 2'-fluoro-5-chloro-2-(3-dimethylcarbamoyl-5-glycylaminomethyl-1H-1,2,4-triazol-1-yl)benzophenone.

6. A compound according to claim 2, namely 5-chloro-2-[3-dimethylcarbamoyl-5-(1-glycylaminoethyl)-1H-1,2,4-triazol-1-yl]benzophenone.

7. A compound according to claim 2, namely 2',5-dichloro-2-(3-dimethylcarbamoyl-5-L-leucylaminomethyl-1H-1,2,4-triazol-1-yl)benzophenone.

8. A compound according to claim 2, namely 2',5-dichloro-2-(3-dimethylcarbamoyl-5-L-phenylalanylaminomethyl-1H-1,2,4-triazol-1-yl)benzophenone.

9. A compound according to claim 1, in which R is lower alkoxy, pyrrolidino, piperidino, or morpholino; and $$R^7-\underset{|}{N}-R^8$$

is amino.

10. A compound according to claim 9, namely 2',5-dichloro-2-(3-pyrrolinocarbonyl-5-glycylaminomethyl-1-H-1,2,4-triazol-1-yl)benzophenone.

11. A compound according to claim 9, namely 2',5-dichloro-2-(3-morpholinocarbonyl-5-glycylaminomethyl-1H-1,2,4-triazol-1-yl)benzophenone.

12. A compound according to claim 9, namely 4-bromo-2-(2-picolinoyl)-1-(3-pyrrolidinocarbonyl-5-glycylaminomethyl-1H-1,2,4-triazol-1-yl)benzene.

13. A compound according to claim 9, namely 2',5-dichloro-2-(3-ethoxycarbonyl-5-glycylaminomethyl)-1H-1,2,4-triazol-1-yl)benzophenone.

14. A compound according to claim 1, in which R is dimethylamino; and

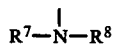

is methylamino, dimethylamino, or pyrrolidino.

15. A compound according to claim 14, namely 2',5-dichloro-2-[3-dimethylcarbamoyl-5-(2-dimethylaminoacetyl)aminomethyl-1H-1,2,4-triazol-1-yl]benzophenone.

16. A compound according to claim 14, namely 2',5-dichloro-2-[3-dimethylcarbamoyl-5-(2-pyrrolidinoacetyl)aminomethyl-1H-1,2,4-triazol-1-yl]benzophenone.

17. A compound according to claim 14, namely 2',5-dichloro-2-[3-dimethylcarbamoyl-5-(2-methylaminoacetyl)aminomethyl-1H-1,2,4-triazol-1-yl]benzophenone.

* * * * *